United States Patent [19]

Mentrup et al.

[11] 3,937,708
[45] Feb. 10, 1976

[54] N-PHENYL-IMIDAZOLIDINE-1-ONES
[75] Inventors: Anton Mentrup; Ernst-Otto Renth; Kurt Schromm, all of Ingelheim am Rhein; Peter Danneberg, Ockenheim, all of Germany
[73] Assignee: Boehringer Ingelheim GmbH, Ingelheim am Rhein, Germany
[22] Filed: Feb. 8, 1974
[21] Appl. No.: 440,823

Related U.S. Application Data
[63] Continuation of Ser. No. 259,532, June 5, 1972, abandoned.

[30] Foreign Application Priority Data
June 7, 1971   Austria ................................. 4920/71

[52] U.S. Cl. .................. 260/268 PH; 260/268 BC; 260/268 BQ; 260/268 H; 424/250
[51] Int. Cl.² ..................................... C07D 295/12
[58] Field of Search ... 260/268 PH, 268 H, 268 BQ, 260/268 BC

[56] References Cited
UNITED STATES PATENTS
3,196,152   7/1965   Wright, Jr. et al............... 260/247.2
3,374,237   3/1968   Wright, Jr. et al. .......... 260/268 PH Primary Examiner—Donald G. Daus
Assistant Examiner—Jose Tovar
Attorney, Agent, or Firm—Hammond & Littell

[57] ABSTRACT
Compounds of the formula

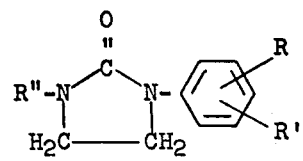

wherein

R is hydrogen, halogen, lower alkyl or lower alkoxy,
R' is   —CHR₁—Q—A,   —CHR₂—A   or —O—CHR₂—CHR₁—Q—A, each in m- or p-position,
where
A is

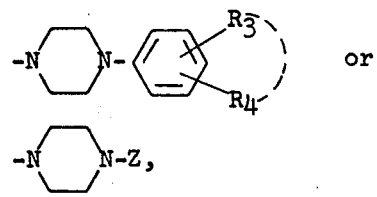

Q is straight or branched alkylene of 1 to 4 carbon atoms,
R₁ is hydrogen, hydroxyl, lower alkoxy or —O—CO—R₅,
R₂ is hydrogen or methyl,
R₃ and R₄, which may be identical to or different from each other, are each hydrogen, lower alkyl, lower alkoxy, halogen, trifluoromethyl or, together with each other and neighboring carbon atoms of the phenyl ring to which they are attached, form a saturated or unsaturated carbocyclic 5- to 6-membered ring,
R₅ is lower alkyl, halo-lower alkyl, hydroxy-lower alkyl, lower alkoxy-lower alkyl, amino, (mono-lower alkyl)-amino or (di-lower alkyl)-amino,
Z is an aromatic heterocyclic ring with one to two heteroatoms, which may optionally be condensed with a benzene ring, and
R'' is hydrogen, straight or branched lower alkyl, lower alkenyl, lower alkynyl, hydroxy-lower alkyl, (di-lower alkyl)-amino-lower alkyl or aralkyl, and their non-toxic, pharmacologically acceptable acid addition salts; the compounds as well as their salts are useful as CNS-depressants, neuroleptics, analgesics, antiphlogistics, spasmolytics, broncholytics, hypotensives and anti-cholesteremics.

5 Claims, No Drawings

N-PHENYL-IMIDAZOLIDINE-1-ONES

This is a continuation of copending application Ser. No. 259,532, filed June 5, 1972, now abandoned.

This invention relates to novel N-phenyl-imidazolidine-2-ones, as well as to various methods of preparing these compounds.

More particularly, the present invention relates to a novel class of N-phenyl-imidazolidine-2-ones represented by the formula

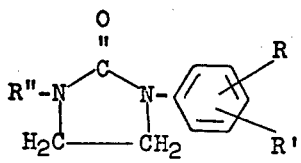

(I)

wherein
R is hydrogen, halogen, lower alkyl or lower alkoxy,
R' is —CHR$_1$—Q—A, —CHR$_2$—A or —O—CHR$_2$—CHR$_1$—Q—A, each in m- or p-position,
where
A is -N⟨ ⟩N-⟨phenyl with R$_3$, R$_4$⟩  or

-N⟨ ⟩N-Z,

Q is straight or branched alkylene of one to four carbon atoms,
R$_1$ is hydrogen, hydroxyl, lower alkoxy or —O—CO—R$_5$,
R$_2$ is hydrogen or methyl,
R$_3$ and R$_4$, which may be identical to or different from each other, are each hydrogen, lower alkyl, lower alkoxy, halogen, trifluoromethyl or, together with each other and neighboring carbon atoms of the phenyl ring to which they are attached, form a saturated or unsaturated carbocyclic 5- to 6-membered ring,
R$_5$ is lower alkyl, halo-lower alkyl, hydroxy-lower alkyl, lower alkoxy-lower alkyl, amino, (mono-lower alkyl)-amino or (dilower alkyl)-amino,
Z is an aromatic heterocyclic ring with one to two heteroatoms, which may optionally be condensed with a benzene ring, and
R'' is hydrogen, straight or branched lower alkyl, lower alkenyl, lower alkynyl, hydroxy-lower alkyl, (di-lower alkyl)-amino-lower alkyl or aralkyl, and non-toxic, pharmacologically acceptable acid addition salts thereof.

The compounds embraced by formula I above may be prepared by the following methods:

Method A

By reacting an N-substituted piperazine of the formula

H — A   (II)

wherein A has the same meanings as in formula I, with an N-phenyl-imidazolidine-2-one of the formula (III)

wherein
R and R'' have the same meanings as in formula I, and
R$_a$ is —CHR$_2$—X, —CHR$_1$—Q—X or —O—CHR$_2$—CHR$_1$—Q—X, each in m- or p-position,
where X is an anion which is capable of combining with the hydrogen atom of the piperazine derivative of the formula II and being split off as an acid of the formula H-X, such as halogen, —O—SO$_2$—alkyl or O—SO$_2$—aryl,
in the presence of an H-X-binding agent, such as potassium carbonate, sodium carbonate or a sufficient excess of the piperazine derivative of the formula II.

Method B

For the preparation of a compound of the formula I wherein R$_1$ is hydrogen, hydroxyl or lower alkoxy, by subjecting a urea derivative of the formula (IV)

wherein R, R' and R'' have the same meanings as in formula I, and X has the meanings defined in formula III, to ring closure through heating in the presence of a strong base, such as potassium hydroxide or sodium hydroxide.

Method C

For the preparation of a compound of the formula I wherein R'' is other than hydroxy-lower alkyl, R$_1$ is other than hydroxyl and R$_5$ is other than hydroxy-lower alkyl, amino or (mono-lower alkyl)-amino, by subjecting an ethylenediamine derivative of the formula

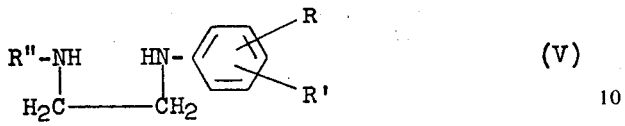 (V)

wherein R, R' and R'' have the same meanings as in formula I, to ring closure with a suitable carbonic acid derivative, especially with phosgene, a chlorocarbonic acid ester, a carbonic acid ester, N,N'-carbonyldiimidazole or urea, or with a metal cyanate in the presence of an acid.

However, instead of starting from an amine of the formula V, it is also possible to start from an intermediate, such as a carbamate, a urea or a carbamic acid chloride, and subject it to ring closure.

Method D

For the preparation of a compound of the formula I wherein A is

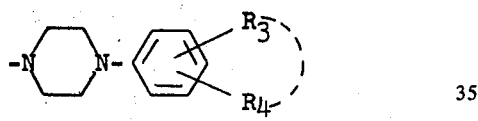

wherein $R_3$ and $R_4$ have the meanings defined above, by reductive amination of an N-phenyl-imidazolidine-2-one of the formula

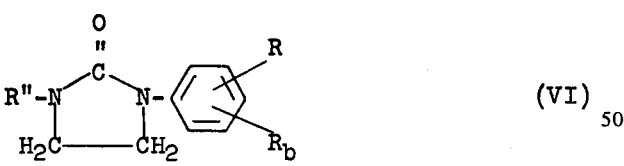 (VI)

wherein
R and R'' have the same meanings as in formula I, and
$R_b$ is —CHO, —CHR$_1$, —C$_n$G$_{2n-1}$O or —O —CH-R$_2$—CHR$_1$—C$_n$H$_{2n-1}$O, each in m- or p-position,
where
$R_1$ and $R_2$ have the same meanings as in formula I, and
$n$ is 1, 2, 3 or 4,
with a piperazine derivative of the formula II and catalytically activated hydrogen.

Method E

For the preparation of a compound of the formula I wherein R' is —CH(OH)—Q—A, by reducing a ketone of the formula

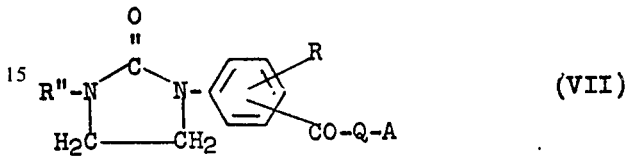 (VII)

wherein R, R'', Q and A have the same meanings as in formula I, preferably with a complex hydride such as sodium borohydride, or also with catalytically activated hydrogen.

Method F

For the preparation of a compound of the formula I wherein $R_1$ is hydrogen and R'' is lower alkyl, hydroxy-lower alkyl or aralkyl, by removing the hydroxyl group from an N-phenyl-imidazolidine-2-one of the formula

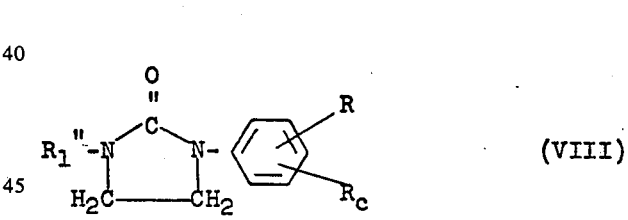 (VIII)

wherein
R has the same meanings as in formula I,
$R_1''$ is lower alkyl, lower alkoxy-lower alkyl or aralkyl, and
$R_c$ is —CR$_2$(OH)——A, —CH(OH)—Q—A or —O—CHR$_2$—CH(OH)—Q—A, each in m- or p-position,
preferably by first replacing the hydroxyl group by chlorine with the aid of a chlorinating agent, such as $SOCl_2$ or $PCl_5$, and then hydrogenating the chlorinated intermediate.

Method G

For the preparation of a compound of the formula I wherein $R_1$ is hydroxyl, by reacting an N-phenyl-imidazolidine-2-one of the formula

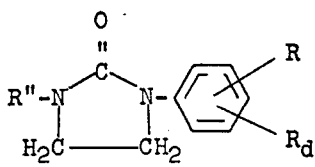 (IX)

wherein
R and R'' have the same meanings as in formula I, and
$R_d$ is

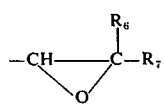

or

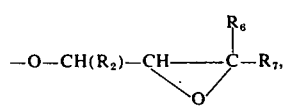

each in m- or p-position,
where $R_6$ and $R_7$ are hydrogen or alkyl comprising a total of no more than three carbon atoms,
with a piperazine derivative of the formula II.

Method H

For the preparation of a compound of the formula I wherein $R_1$ is hydrogen, lower alkoxy or —O—CO—$R_5$, where $R_5$ is lower alkyl, lower alkoxy-lower alkyl or (di-lower alkyl) amino, by reacting an N-phenyl-imidazolidine-2-one derivative of the formula

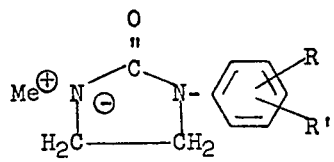 (X)

wherein
R has the same meanings as in formula I,
R' has the same meanings as in formula I except that $R_1$ has the limited meanings defined above, and
Me⁺ is an alkali metal cation,
with a compound of the formula $$R'' - X \qquad (XI)$$

wherein
R'' has the same meanings as in formula I, and
X has the same meanings as in formula III.
The compound of the formula X may be obtained from the corresponding nor-compound by metallization with, for example, sodium hydride, lithium amide, potassium tert.butylate or the like.

Method I

For the preparation of a compound of the formula I wherein R' is —O—$CHR_2$—$CH_2$—Q—A, by reacting a phenol of the formula

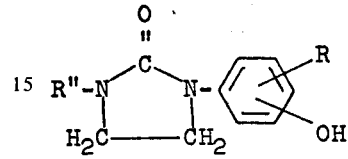 (XII)

wherein R and R'' have the same meanings as in formula I and the phenolic hydroxyl group is in the m- or p-position, with a compound of the formula $$X—CHR_2—CH_2—Q—A \qquad (XIII)$$

wherein $R_2$, Q and A have the same meanings as in formula I and X has the meanings defined in connection with formula III, in the presence of an HX-binding agent, such as sodium carbonate or potassium carbonate.

Method J

For the preparation of a compound of the formula I wherein $R_1$ is lower alkoxy or —O—CO—$R_5$ and R'' is other than hydroxy-lower alkyl, by reacting an N-phenyl-imidazolidine-2-one derivative of the formula

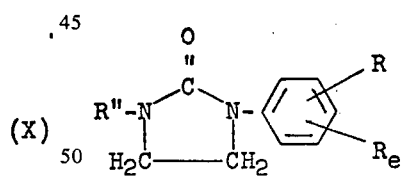 (XIV)

wherein
R and R'' have the same meanings as in formula I, and $R_e$ is —CH(OH)—Q—A or —O—CH($R_2$)—CH(OH)—Q—A, each in m- or p-position,
where $R_2$, Q and A have the same meanings as in formula I,
with a reagent suitable for replacement of the OH-hydrogen by alkyl or —CO—$R_5$, that is, with a conventional alkylating agent, such as an alkyl halide, a dialkyl sulfate or an alkyl sulfonate, in the presence of an alkali under ether-forming conditions. However, the same ether substitution operation may also be effected by first replacing the OH-group in substituent $R_e$ with chlorine by means of a chlorinating agent, such as PCl₅ or SOCl₂, and subsequently reacting the chlorinated compound with an alkali metal alcoholate.

The introduction of the —CO—R₅ group is effected by means of a corresponding acylating agent, such as carboxylic acid chloride, a carbamoyl chloride or a carboxylic acid anhydride; in those instances where R₅ is to be lower alkyl, halo-lower alkyl or lower alkoxy-lower alkyl, a compound of the formula XIV may also be reacted with the corresponding carboxylic acid in the presence of a condensation agent, such as dicyclohexyl-carbodiimide or carbonyldiimidazole.

Furthermore, if R₅ is to be methyl, amino or (mono-lower alkyl)-amino, the introduction of the —CO—R₅ substituent may also be effected by subjecting a compound of the formula II to an addition reaction with ketene, cyanic acid or a lower alkyl isocyanate.

The starting compounds needed for methods A through J are either known compounds or may be prepared by conventional methods.

The compounds embraced by formula I occur as racemic mixtures or as optically active isomers, such as antipode pairs or diastereomeric pairs; to the extent that these compounds occur as racemates or diastereomeric antipode pairs, these may be separated in conventional manner into the diastereomeric racemates or the individual optical antipodes.

The optically inactive as well as the optically active forms of the compounds of the formula I are organic bases and therefore form acid addition salts with inorganic or organic acids. Examples of non-toxic, pharmacologically acceptable acid addition salts are those formed with hydrochloric acid, hydrobromic acid, sulfuric acid, methanesulfonic acid, acetic acid, propionic acid, citric acid, maleic acid, tartaric acid, 8-chlorotheophylline or the like.

Wherever or whenever we refer to "lower alkyl" or "lower alkoxy" herein, we intend to include generally those of one to four and preferably one to two carbon atoms. Likewise, when we refer to "aryl," we mean preferably phenyl or also naphthyl; "aralkyl" preferably designates benzyl; and chlorine and bromine are preferred meanings of "halogen."

The following examples further illustrate the present invention and will enable others skilled in the art to understand it more completely. It should be understood, however, that the invention is not limited solely to the particular examples given below.

EXAMPLE 1

1-[4'-Imidazolidinon-(2')-ylphenethyl]-4-(3''-chlorophenyl)-piperazine 19.6 gm (0.1 mol) of N-(3-chlorophenyl)-piperazine and 23.0 gm (0.1 mol) of 2-(4'-nitrophenyl)-ethylbromide were refluxed in 150 ml of acetonitrile in the presence of 20 gm of potassium carbonate for 2 hours. The hot solution was vacuum-filtered, the residue was washed with acetonitrile and the combined solutions were concentrated by evaporation. Treatment of the residue with isopropanol yielded 19 gm of 1-(4'-nitrophenethyl)-4-(3''-chlorophenyl)-piperazine (m.p. 87°C) and 4.5 gm more were obtained from the mother liquor.

The total yield was 23.5 gm (70% of theory). The nitro-compound was dissolved in 240 ml of methanol and hydrogenated in the presence of 1 gm of PtO₂ at 20°C and 5 atmospheres gauge of hydrogen until the nitro group has been reduced. After separation of the catalyst, 21 gm of amine were obtained as a distillation residue, which was reacted without further purification with 8.5 gm of β-chloroethylisocyanate in 150 ml of benzene by heating to 50°C for 3 hours, yielding 27 gm (96% of theory), of the following compound:

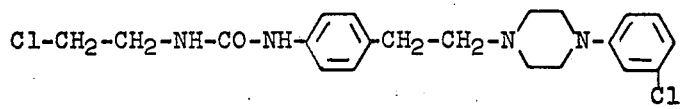

decomposition point above 200°C.

27 gm of this substance were dissoled in 360 ml of hot ethanol, and a solution of 4.0 gm of potassium hydroxide in 40 ml of ethanol was then added. The reaction mixture was refluxed for 3 to 5 minutes and then vacuum-filtered after cooling, and the residue was freed from inorganic matter by extraction with water. 17 gm of the compound of the formula

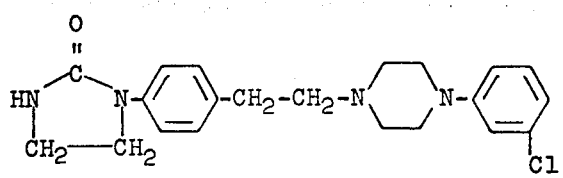

were obtained in the form of the base. For conversion into the salt, the base was heated to boiling in 500 ml of ethanol, and an equivalent quantity of methanesulfonic acid was then added in the form of an ethanolic solution. 20.5 gm of the methanesulfonate, m.p. 239°C (from ethanol), were obtained.

The following compounds were prepared in a manner analogous to that described in Example 1:

TABLE 1

| Example No. | R' | a) Acid/m.p. or decomposition point of the salt [°C]<br>b) M.p. of base [°C] |
|---|---|---|
| 2 | 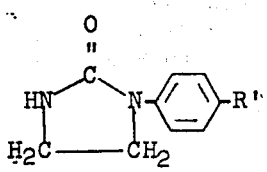 | a) CH₃SO₃H/209<br>b) 180-181 |

TABLE 1 (cont'd)

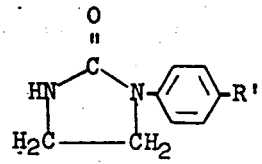

| Example No. | R' | a) Acid/m.p. or decomposition point of the salt [°C]<br>b) M.p. of base [°C] |
|---|---|---|
| 3 | -(CH₂)₂-N(piperazine)N-phenyl-CH₃ (o-CH₃) | a) CH₃SO₃H/211<br>b) 195 |
| 4 | -CHOH-CH₂-N(piperazine)N-phenyl-CH₃ (o-CH₃) | a) CH₃SO₃H/191<br>b) 223 |
| 5 | -(CH₂)₂-N(piperazine)N-phenyl-Cl (o-Cl) | a) CH₃SO₃H/263-265 |
| 6 | -(CH₂)₂-N(piperazine)N-phenyl-Cl (p-Cl) | a) CH₃SO₃H/241 |
| 7 | -(CH₂)₂-N(piperazine)N-C₆H₅ | a) CH₃SO₃H/271 |
| 8 | -(CH₂)₂-N(piperazine)N-phenyl-CF₃ | a) CH₃SO₃H/216-217 |
| 9 | -CH₂-CH(CH₃)-N(piperazine)N-phenyl-CH₃ | a) HCl/299-301 |
| 10 | -(CH₂)₂-N(piperazine)N-phenyl-(CH₃)₂ (3,5) | a) CH₃SO₃H/325 |
| 11 | -(CH₂)₂-N(piperazine)N-phenyl-(CH₃)₂ (3,4) | a) CH₃SO₃H/269-271 |
| 12 | -(CH₂)₂-N(piperazine)N-phenyl-(CH₃)₂ (2,6) | a) HCl/278-280 |

TABLE 1 (cont'd)
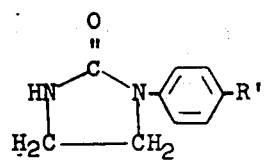
a) Acid/m.p. or decomposition point of the salt [°C]
b) M.p. of base [°C]
| Example No. | R' | |
|---|---|---|
| 13 | 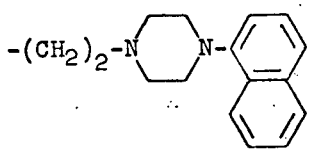 | a) CH₃SO₃H/235-236 |
| 14 | 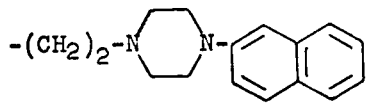 | a) CH₃SO₃H/295-293 |
| 15 | 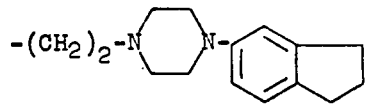 | a) CH₃SO₃H/255-256 |
| 16 | 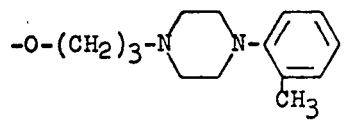 | a) CH₃SO₃H/175 |
| 17 | 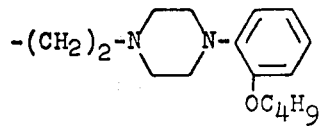 | a) CH₃SO₃H/202 |
| 18 | 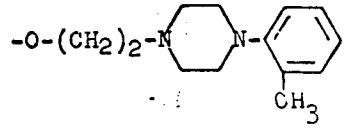 | a) CH₃SO₃H/211<br>b) 152 |
| 19 | 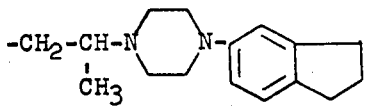 | a) CH₃SO₃H/248-250 |
| 20 | 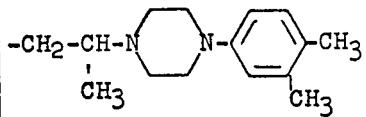 | a) CH₃SO₃H/236-238 |
| 21 | 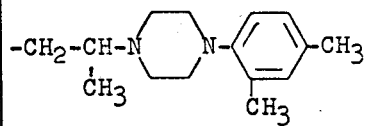 | a) CH₃SO₃H/300-301 |
| 22 | 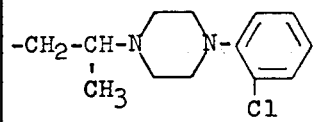 | a) CH₃SO₃H/218 |

TABLE 1 (cont'd)

a) Acid/m.p. or decomposition point of the salt [°C]

| Example No. | R' | b) M.p. of base[°C] |
|---|---|---|
| 23 | -CH$_2$-CH(CH$_3$)-N(piperazine)-naphthyl | a) CH$_3$SO$_3$H/275-279 |
| 24 | -CH$_2$-CH(CH$_3$)-N(piperazine)-naphthyl | a) CH$_3$SO$_3$H/270 |

The following compound was also obtained by a method analogous to that of Example 1:

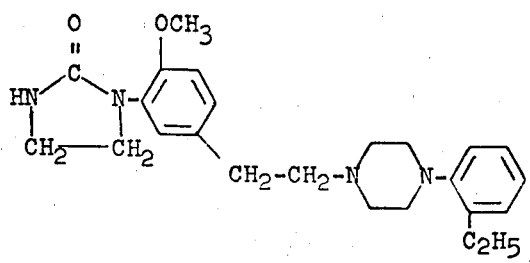

M.p. of its hydrochloride: 256°–257°C.

In the following examples Z denotes the radical

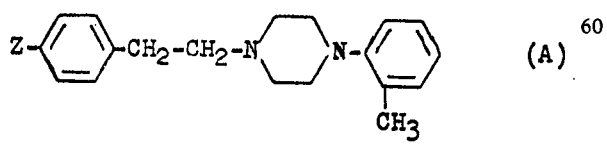

EXAMPLE 25

Z-⟨phenyl⟩-CH$_2$-CH$_2$-N(piperazine)-⟨phenyl-CH$_3$⟩ (A)

28.4 gm (0.1 mol) of 2-[4-imidazolidinon-(2)-yl-phenyl]-ethyl methyl sulfonate, obtained from 2-[4-imidazolidinon-(2)-yl-phenyl]-ethanol and methanesulfochloride in pyridine, were reacted with 17.5 gm of N-(2-methylphenyl)-piperazine in 120 ml of acetonitrile in the presence of 21 gm of sodium hydroxide solution by refluxing for 1 hour. Compound A was isolated as the base, melting point 195°C.

The following compounds were prepared in analogous manner (formula I, R and R'' = H, R' = as indicated):

(1) R' = 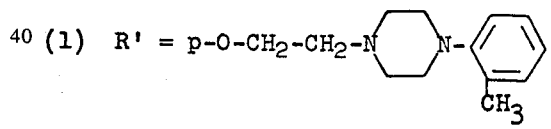

(2) R' = 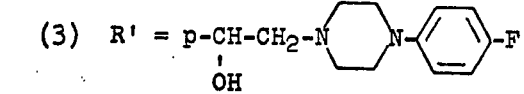

(3) R' = 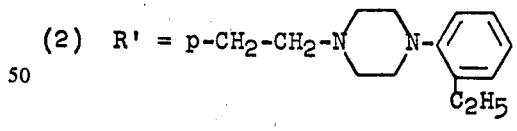

(4) R' = 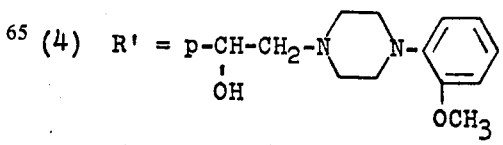

EXAMPLE 26

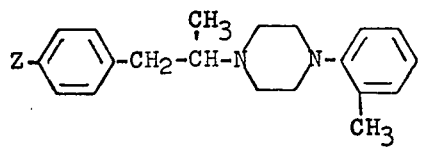 (B)

10 gm of 1-(4'-imidazolidinon-2'-yl-phenyl)-2-oxo-propane were hydrogenated with 8.1 gm of N-(2-methylphenyl)piperazine in 100 ml of methanol in the presence of 1 gm of PtO₂ at 60°C and 5 atmospheres gauge until the calculated quantity of hydrogen had been taken up. After removal of the catalyst, the methanol was distilled off, and the residue was crystallized by the addition of acetonitrile. The hydrochloride of compound B, which melted at 299°–301°C and crystallized as the monohydrate, was obtained from the base in a small quantity of methanol by adding concentrated hydrochloric acid.

The following compounds were prepared in analogous manner (formula I, R and R'' = H, R' = as indicated):

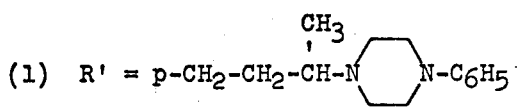

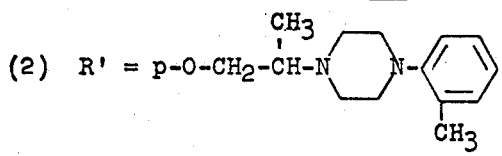

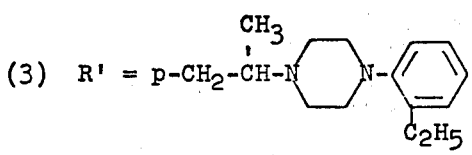

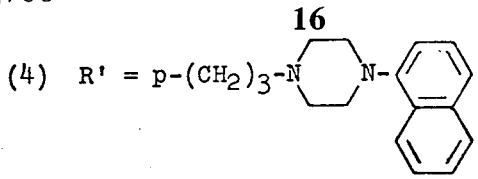

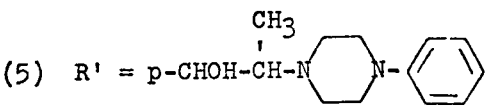

EXAMPLE 27

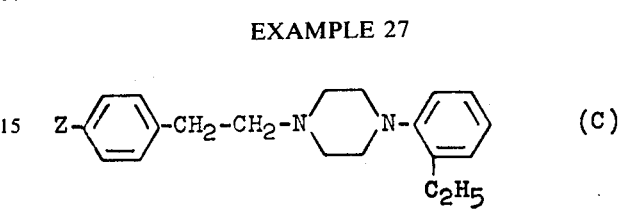 (C)

15.5 gm (0.05 mol) of N-[β-p-aminophenyl)-ethyl]-N'-(o-ethylphenyl)-piperazine, 1.6 gm of paraformaldehyde and a solution of 4.1 gm of potassium cyanide in 7 ml of water were combined in 85 ml of glacial acetic acid at 15° to 20°C, and the mixture was allowed to stand overnight at room temperature. The resulting product of the formula

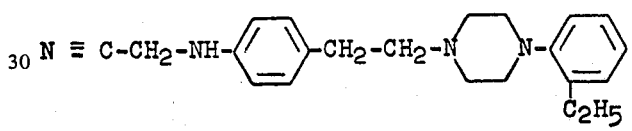

had a melting point of 137°–138°C. It was hydrogenated in methanol, using PtO₂ as the catalyst, to form

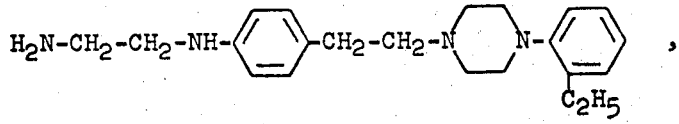, which was treated in benzene with the calculated quantity of N,N'-carbonyldiimidazole dissolved in tetrahydrofuran. The mixture was allowed to stand overnight at room temperature, was then refluxed for 2 hours, and the resulting product C was isolated as the base (m.p. 178°–181°C.

The following compounds were prepared in analogous manner: (formula I, R and R'' = H, R' = as indicated)

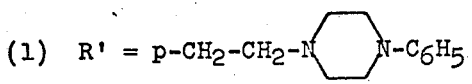

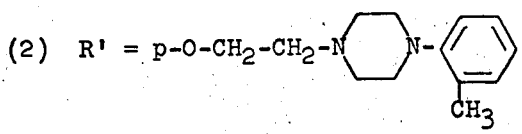

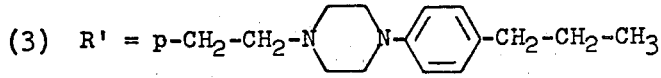

EXAMPLE 28

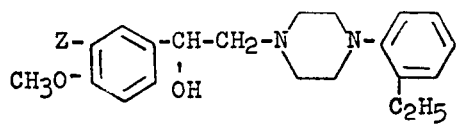 (D)

4-Methoxy-3-nitro-acetophenone was reduced to 4-methoxy-3-amino-acetophenone, which was reacted with β-chloroethyl-isocyanate to form

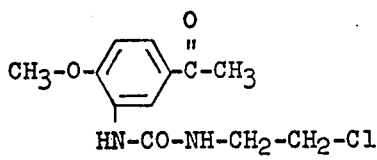

(m.p. 149°C) which was converted into the imidazolidinone derivative of the formula

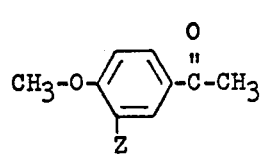

(m.p. 186°–188°C) by reaction with potassium hydroxide in ethanol. Reaction of this compound with bromine in chloroform yielded the compound of the formula

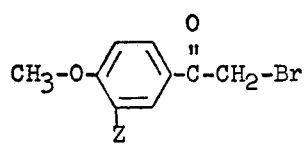

which was reacted as the raw product (85 gm) with 105 gm of N-(2-ethyl-phenyl)-piperazine in 1,500 of acetonitrile to yield the compound of the formula

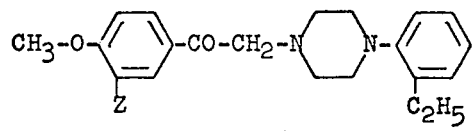

(m.p. 170°–172°C). 5 gm of NaBH₄ was added portionwise to 32 gm of this compound in 250 ml of methanol. The reaction mixture was left to stand overnight and was then worked up, yielding 32.5 gm of compound D in the form of its hydrochloride (m.p. 234°C).

The following compounds were prepared in analogous manner:

(1) 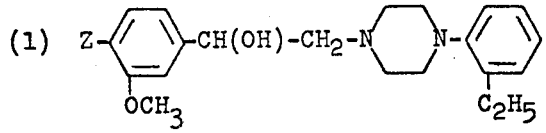

(2) 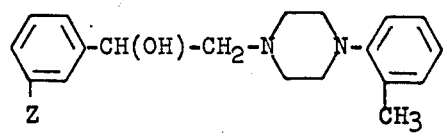

(3) 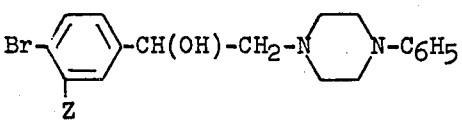

(4) 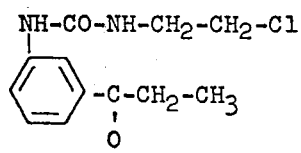

EXAMPLE 29

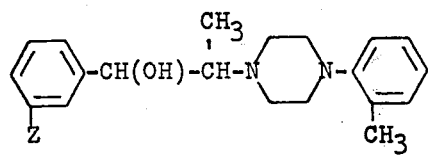 (E, threo- and erythro form)

35 gm of 3-aminopropiophenone in 250 ml of benzene were reacted with 27 gm of β-chloroethyl-isocyanate to yield the compound of the formula

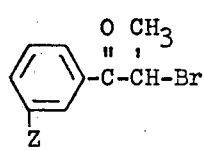

(m.p. 114°C), which was cyclized with potassium hydroxide to form 3-[imidazolidinon-(2)-yl]-propiophenone (m.p. 162°C), which was reacted with bromine in chloroform to yield the bromoketone of the formula (m.p. 181°C).

33 gm of this bromoketone were boiled with 39 gm of N-(2-methyl-phenyl)-piperazine in 660 ml of acetonitrile for 30 minutes, and the reaction mixture was worked up to yield 40 gm of the compound of the formula

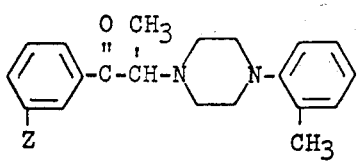 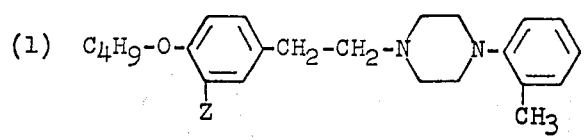

(m.p. 157°C).

6 gm of this aminoketone in 60 ml of ethanol were mixed with 1 gm of NaBH₄, and the mixture was heated to 50°C. After cooling, 1 gm of NaBH₄ was again added. 5 gm of the threo-form of compound E (m.p. 204°C) crystallized after about one hour. M.p. of its methane sulfonate: 241°C.

To prepare the erythro-form of compound E, 6 gm of the aminoketone were dissolved in methanol and hydrogenated with palladium/charcoal at 60°C and 5 atmospheres gauge. Working up yielded the erythro-form of compound E, m.p. 161°C.

EXAMPLE 30

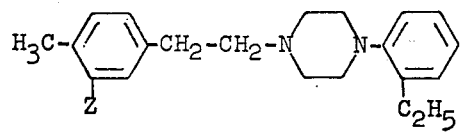 (F)

5 gm of the compound of the formula

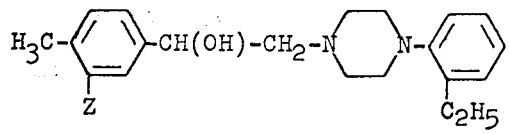 · HCl

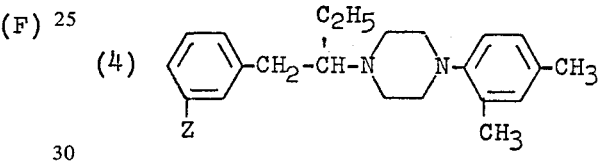

were added portionwise to 20 ml of thionyl chloride; the resulting solution turned red after some time. The excess thionyl chloride was distilled off, and the residue was brought to crystallization by the addition of acetonitrile and boiling. 3.3 gm of the compound of the formula

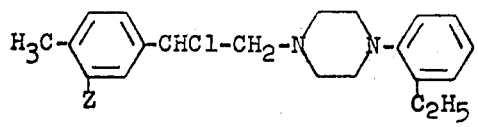 · HCl

EXAMPLE 31

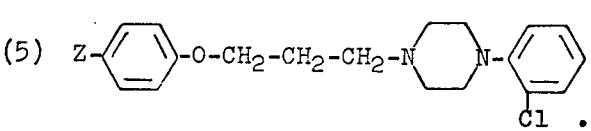 (G)

where thereby obtained, which were hydrogenated in the pressence of 1.67 gm of dimethylaniline and Raney nickel as the catalyst in methanol until the absorption of hydrogen ceased. After removal of dimethylaniline by distillation, compound F was isolated from the residue as its hydrochloride, m.p. 256°–257°C.

The following compounds were prepared in analogous manner;

4-Amino-acetophenone was converted into 4-[imidazolidinon-(2')-yl]-acetophenone (m.p. 208°C) by reaction with β-chloroethyl-isocyanate, followed by treatment with potassium hydroxide. The ω-bromoketone of the formula

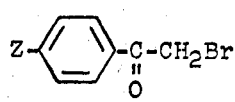

was obtained in chloroform by the addition of 1 mol of bromine. M.p. 175°C.

2 gm of sodium borohydride were slowly added to 14.2 gm of the bromoketone in 200 ml of ethanol while cooling with ice, and the reaction mixture was then stirred for two hours at room temperature. Precipitated sodium bromide was removed by vacuum filtration, 0.5 ml of water and 17.6 gm of N-2-methylphenylpiperazine were added to the filtrate, and the mixture was left to stand overnight at room temperature and was then refluxed for two hours. Compound (G) was then isolated; it had a melting point of 221°–223°C.

The following compounds were prepared in analogous manner:

(1) 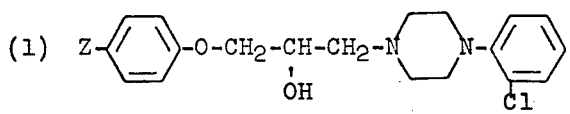

(2) 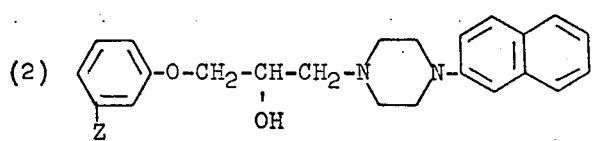

(3) 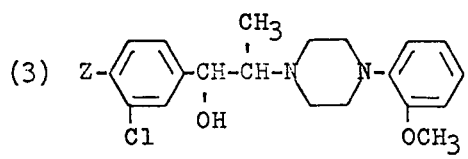

EXAMPLE 32

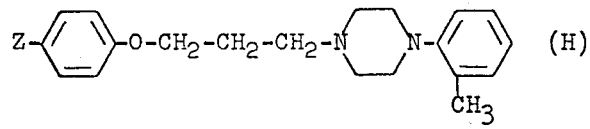 (H)

4-Benzyloxy-aniline was reacted with β-chloroethylisocyanate to produce the compound of the formula

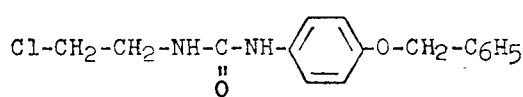

(m.p. 176°C), which was converted with potassium hydroxide in ethanol into the imidazolidinone derivative of the formula

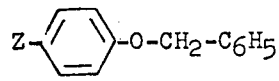

(m.p. 226°C).

Catalytic hydrogenation of the latter yielded the compound of the formula

m.p. 180°C.

14.2 gm of this phenol were reacted in ethanol with 12.6 gm of N-(3-chloropropyl)-N'-(2-methylphenyl)-piperazine by boiling in the presence of 3.1 gm of potassium hydroxide to yield compound H (m.p. 171°C).

The following compounds were prepared in analogous manner:

(1) 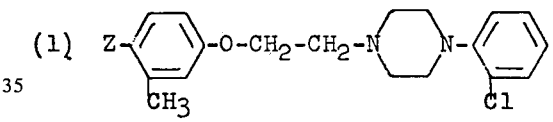

(2) 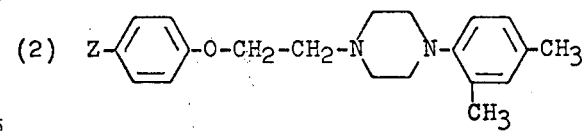

EXAMPLE 33

N-[4-Imidazolidinon-(2)-yl-phenylmethyl]-N'-phenyl-piperazine

N-Phenyl-N'-(4-nitro-benzyl)-piperazine was prepared from 4-nitro-benzyl bromide and N-phenyl-piperazine by refluxing in acetonitrile. Reduction of this compound with hydrogen/PtO₂ in methanol yielded N-phenyl-N'-(4-amino-benzyl)-piperazine (m.p. 105°C), which was reacted with β-chloroethyl- isocyanate in benzene to yield the compound of the formula

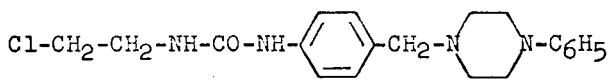

21 gm of this compound were mixed with 2.4 gm of NaOH in 160 ml of ethanol, and the mixture was refluxed for 10 minutes. 16 gm of the compound named in the heading of this example were obtained by isolation from ethanol (m.p. 218°C). Its methanesulfonate (m.p. 210°C) was obtained from the base with the calculated quantity of methanesulfonic acid in ethanol.

The following compounds were prepared in analogous manner:

(1) 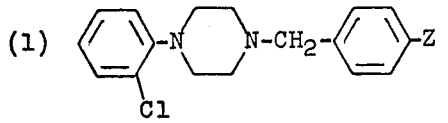

(2) 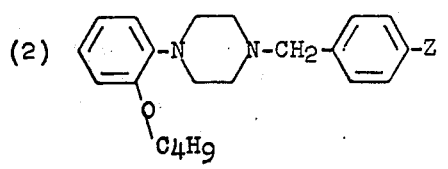

(3) 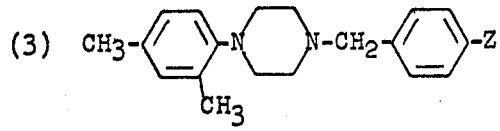

(4) 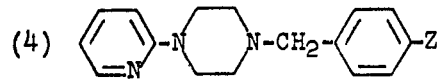

(5) 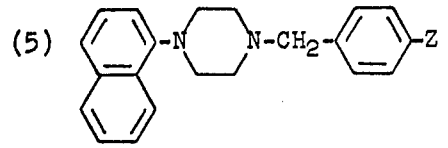

(6) 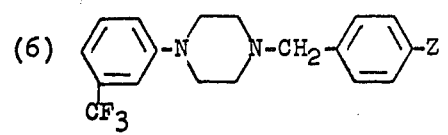

EXAMPLE 34

N-[4'-Imidazolidinon-(2)-yl-phenethyl]-N'-(2''-quinolyl)-piperazine 9 gm of N-(2-quinolyl)-piperazine and 9.7 gm of p-nitro-phenethyl bromide were refluxed for 4 hours in the presence of 12 gm of sodium hydroxide in 125 ml of acetonitrile. The solution was vacuum-filtered while hot, and the residue was washed with acetonitrile. N-(2-quinolyl)-N'-(p-nitrophenethyl)-piperazine crystallized out of the mother liquor on cooling. The yield after vacuum filtration and recrystallization from acetonitrile was 11 gm (m.p. 162°C). 20 gm of this nitro-compound, dissolved in 1 liter of methanol, were hydrogenated at 20°C and 5 atmospheres gauge in the presence of 1 gm of PtO₂ until the theoretical amount of hydrogen had been absorbed. After removal of the catalyst by filtration and concentration of the solvent by evaporation, the crystalline distillation residue was recrystallized from acetonitrile, yielding 18 gm of the corresponding aminocompound (m.p. 133°C). 10 gm of this amino-compound were reacted with 3.8 gm of β-chloroethyl-isocyanate in 200 ml of chloroform by heating for 1 hour at 50°C to yield the compound of the formula

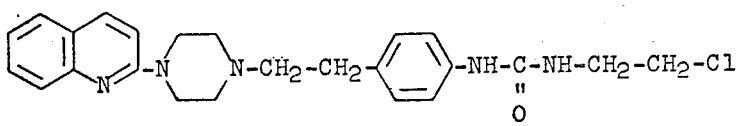

m.p. 233°C. Ring closure was effected by suspending 11 gm of this compound in 165 ml of methanol and then at the boiling point, adding a solution of 1.05 gm of NaOH in 15 ml of H₂O. A solution was formed and crystallization took place after 2 minutes. After cooling and vacuum filtration, the crystals were washed with water and acetonitrile. 7 gm of the compound named in the heading of this example were obtained; m.p. 230°C (from dimethylformamide). The base was converted into the di-methanesulfonate by reaction with the calculated quantity of methanesulfonic acid in alcohol and recrystallization from methanol. The di-methanesulfonate contained 1 mol of water of crystallization; m.p. 197°C.

EXAMPLE 35

N-[1-(4'-Imidazolidinon-(2)-yl-phenyl)-1-hydroxyethyl]-N'-(2''-pyridyl)-piperazine 14.5 gm of 4-[imidazolidinon-(2)-yl]-ω-bromoacetophenone (m.p. 175°C) were refluxed with 16.3 gm of N-(α-pyridyl)-piperazine in 150 ml of acetonitrile for 45 minutes. After separation of the precipitated N-(α-pyridyl)-piperazine hydrobromide, the compound of the formula

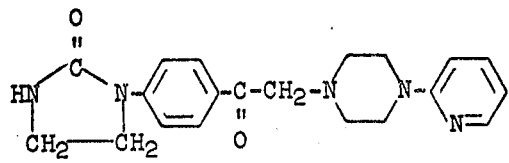

was isolated as the base (76% of theory); m.p. 214°C (from ethanol).

Reduction of this ketone with NaBH₄ in 90% methanol resulted in the corresponding hydroxyl compound with a yield of 88.5%; m.p. 218°C (from ethanol).

EXAMPLE 36

N-(4'-Imidazolidinon-(2)-yl-phenethyl)-N'-(2''-pyridyl)-piperazine 14.1 gm of N-(4-aminophenethyl)-N'-(2'-pyridyl)-piperazine, 1.6 gm of paraformaldehyde and a solution of 4.1 gm of potassium cyanide in 7 ml of water were combined in 85 ml of glacial acetic acid at 15 to 20°C, and the reaction was allowed to go to completion by leaving the reaction mixture to stand overnight at room temperature. The resulting cyanomethylamino-compound was hydrogenated to the corresponding ethylene-diamino derivative with hydrogen in methanol, using PtO₂ as the catalyst. The calculated quantity of N,N'-carbonyl diimidazole, dissolved in tetrahydrofuran, was added to this ethylenediamino derivative in benzene. The reaction mixture was left to stand overnight at room temperature and was then refluxed for 2 hours, yielding the compound of the formula

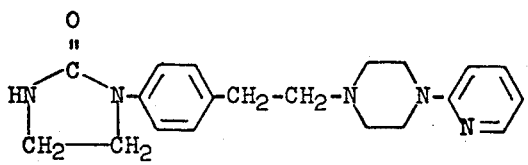

which was isolated as the base; m.p. 200°C.

The following compounds were prepared by methods analogous to those described in Examples 34–36.

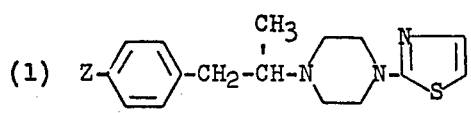

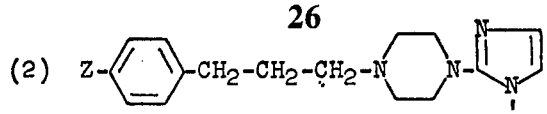

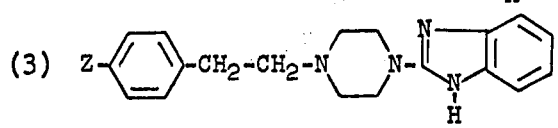

EXAMPLE 37

N-[4'-(3-Methylimidazolidinon-(2)-yl)-phenethyl]-N'-(o-methylphenyl)-piperazine 14.5 gm of N-(4'-imidazolidinon-(2)-yl-phenethyl)-N'-phenyl-piperazine were added to 1.82 gm of NaH (50% in oil) in 250 ml of diglyme. The theoretical quantity of hydrogen had been formed after 1 hour's stirring at 60°C. After the solution had been cooled to 20°C, 5.7 gm of methyl iodide dissolved in 20 ml of absolute diglyme were added dropwise, whereby sodium iodide precipitated out.

After 1 hour's stirring at 50°C, the sodium iodide was removed by vacuum filtration, and the solvent was distilled off. The crystalline residue was washed with ethanol and separated by vacuum filtration and had a melting point of 129°C after recrystallization from ethanol. Yield: 12 gm of the compound named in the heading of this example in the from of the base.

The methanesulfonate was prepared from the base with the calculated quantity of methanesulfonic acid in ethanol; m.p. 196°C (from ethanol).

The following compounds were prepared in an analogous manner:

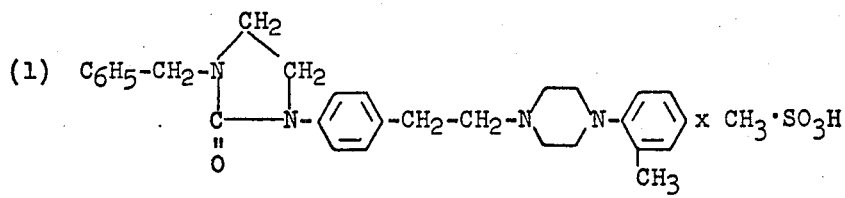

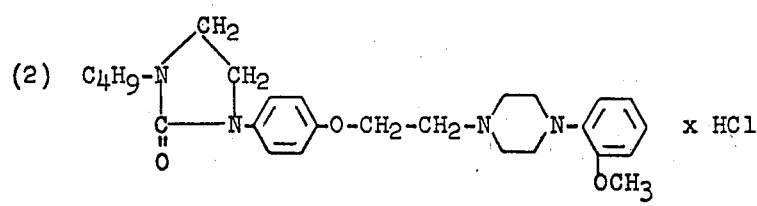

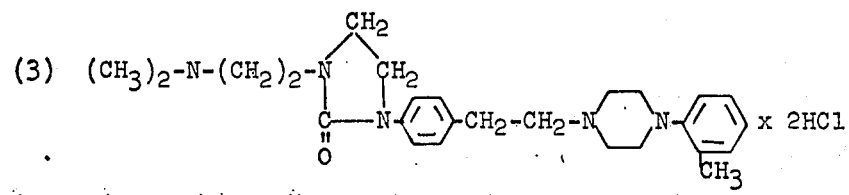

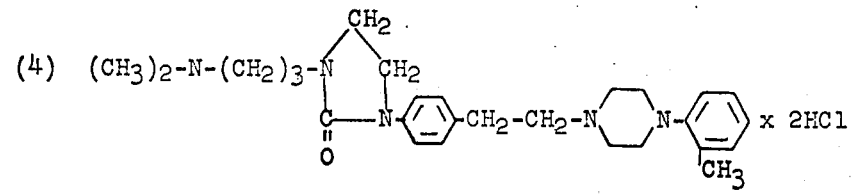

(5) 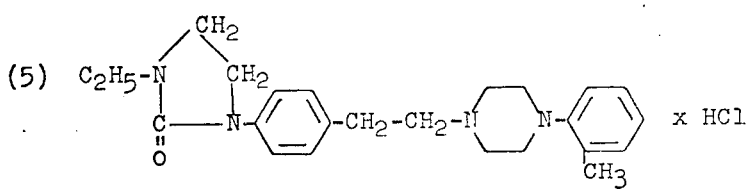
(6) 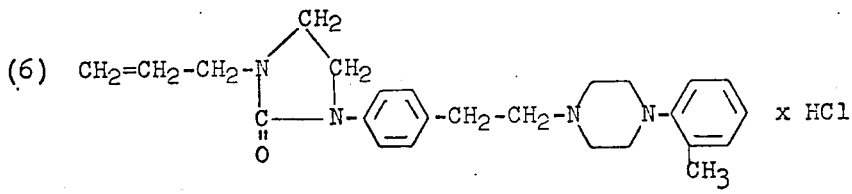
(7) 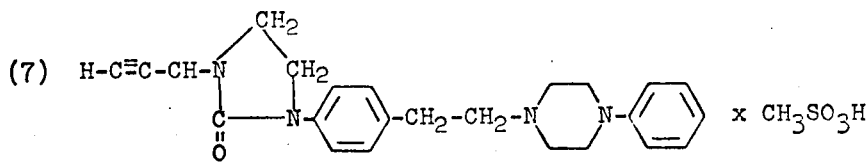
(8) 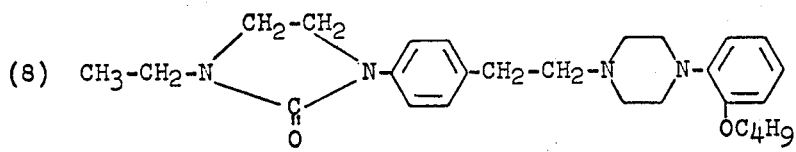
(9) 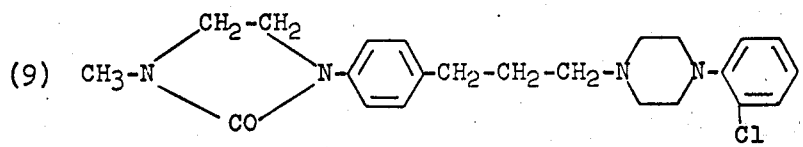
(10) 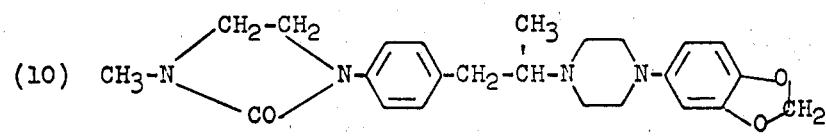
(11) 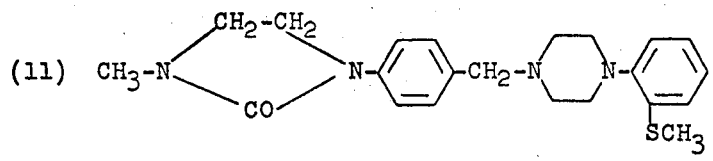
(12) 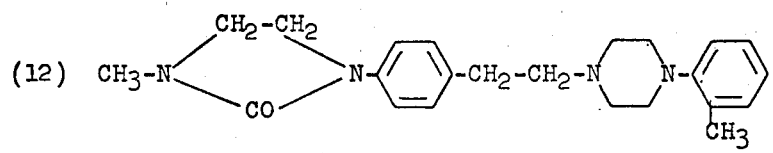
EXAMPLE ''
N-[4'-(3-n-butylimidazolidinon-(2)-yl)-phenethyl]-N'-(o-methylphenyl)-piperazine
28.5 gm of the compound of the formula
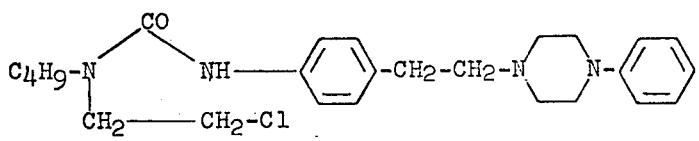
were dissolved in 400 ml of hot ethanol, and an ethanolic solution of 4.0 gm of potassium hydroxide was added. The reaction mixture was refluxed for 5 minutes, and the compound named in the heading was then isolated. M.p. of its hydrochloride: 283°C (from ethanol).

EXAMPLE 39

N-[1-(4''-imidazolidinon-(2')-yl-phenyl)-1-acetoxyethyl]-N'-(o-methylphenyl)-piperazine A mixture consisting of 7.6 gm (0.02 mol) of N-[1-(4''-imidazolidinon-(2')-yl-phenyl)-1-hydroxyethyl]-N'-(o-methylphenyl)-piperazine, 2.5 ml of acetic acid anhydride and 76 ml of chloroform was refluxed for 2 hours. After removal of the solvent by distillation, the residue was crystallized with ethanol and then dissolved in chloroform, and the solution was extracted with potassium carbonate solution and water. The organic phase was dried with sodium sulfate, and the chloroform was distilled off. The raw free base named in the heading of this example remained as a residue. The hydrochloride was obtained from the base by the addition of concentrated hydrochloric acid in hot ethanol. After recrystallization from ethanol the salt had a melting point of 310°C (decomposition). The yield was 5.5 gm.

EXAMPLE 40

N-[1-(4''-Imidazolidinon-(2')-yl-phenyl)-1-methylcarbamoyloxyethyl]-N'-(o-methylphenyl)-piperazine A mixture consisting of 7.6 gm (0.02 mol) of N-[1-(4''-imidazolidinon-2')-yl-phenyl)-1-hydroxy-ethyl]-N'-(o-methylphenyl)-piperazine, 1.1 ml of methyl isocyanate and 114 ml of chloroform was shaken in a montejus for 1 hour at 60°–70°C. After removal of the chloroform by distillation, the raw free base named in the heading of this example was left as a residue. The base, dissolved in hot ethanol, was converted into its hydrochloride by the addition of ethanolic hydrochloric acid. After recrystallization from ethanol, the salt had a melting point of 159°C (decomposition). The yield was 7.5 gm.

EXAMPLE 41

N-[1-(4''-Imidazolidinon-(2')-yl-phenyl)-1-ethoxyethyl]-N'-(o-methylphenyl)-piperazine 8.7 gm (0.02 mol) of N-[1-(4''-imidazolidinon-(2')-yl-phenyl)-1chloro-ethyl]-N'-(o-methylphenyl)-piperazine hydrochloride, prepared from the corresponding hydroxyl compound by chlorination with PCl$_5$ in acetonitrile, were introduced into a solution of 1.84 gm (0.08 mol) of sodium in 200 ml of absolute ethanol. After 1 hour's stirring at 40°C, the calculated quantity of ethanolic hydrochloric acid was added, the precipitated NaCl was removed by vacuum filtration, and the ethanol distilled out to a residual volume of 20 ml. The base was obtained from the residue. Crystallization of the base from ethanol with the calculated quantity of methanesulfonic acid yielded the methanesulfonate of the compound named in the heading of this example.

The following compounds are prepared by methods analogous to those of Examples 39–41:

(1) 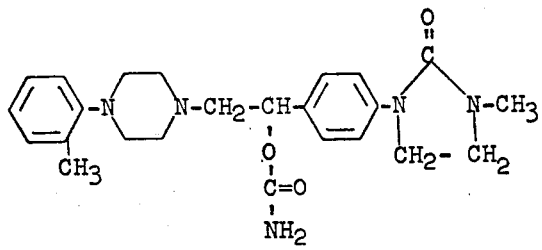

(2) 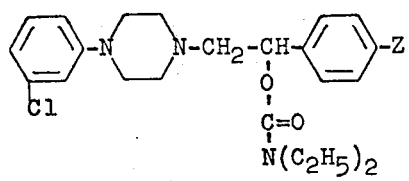

(3) 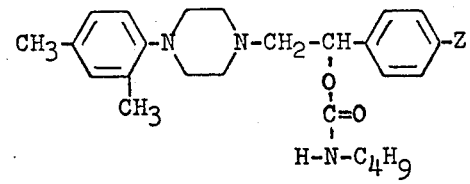

(4) 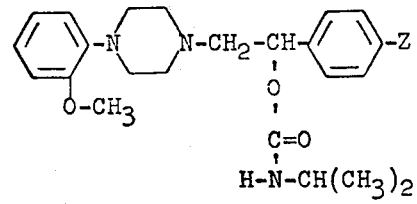

(5) 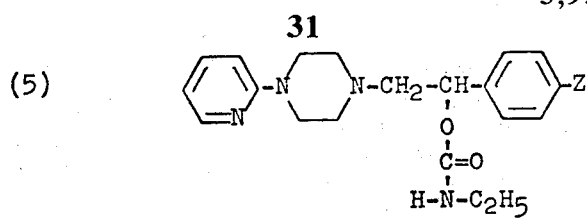
(6) 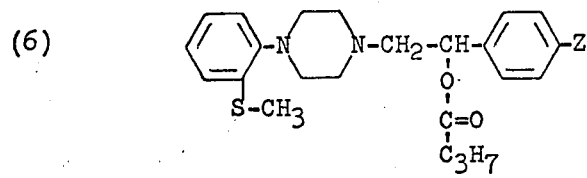
(7) 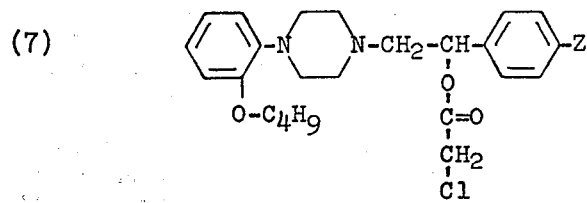
(8) 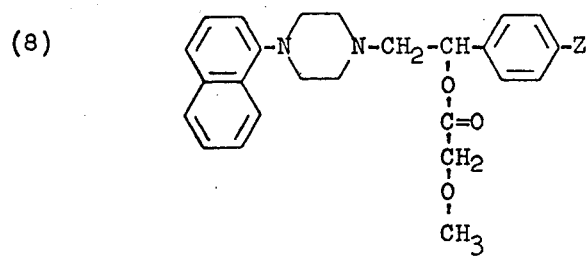
(9) 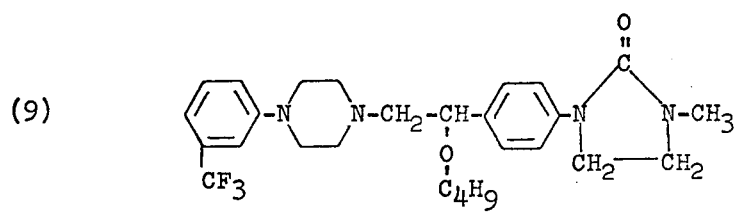
(10) 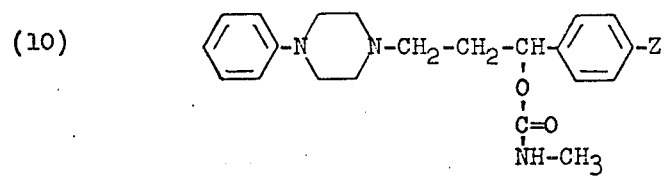
(11) 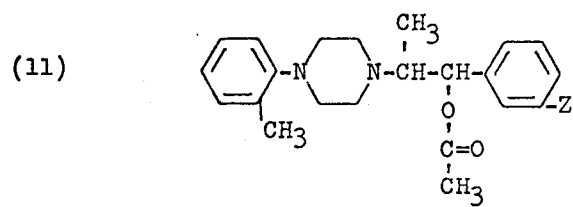
(12) 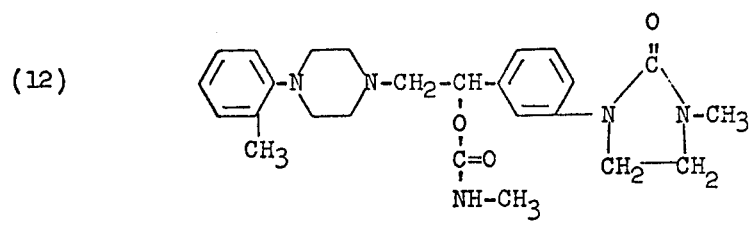

The compounds according to the present invention, that is, those embraced by formula I and their non-toxic, pharmacologically acceptable acid addition salts, in both the optically inactive and optically active forms, have useful pharmacodynamic properties. More particularly, the compounds of the present invention exhibit CNS-depressing, neuroleptic, and anti-cholesteremic activities in warm-blooded animals, such as mice, rats, guinea pigs, dogs and cats.

Particularly effective are, inter alia, N-[4″-imidazolidinon-(2′)-yl-phenethyl]-N′-(o-ethyl-phenyl)-piperazine and N-[4″-imidazolidinon-(2′)-yl-phenethyl]-N′-(o-methyl-phenyl)-piperazine, as well as those compounds of the formula I wherein R″ is hydrogen and $R_1$ is hydrogen or hydroxyl, and their non-toxic acid addition salts.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, aerosols, suppositories and the like. One effective dosage unit of the compounds according to the present invention is from about 0.026 to 1.35 mgm/kg body weight, preferably from 0.066 to 0.67 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 42

Tablets

The tablet composition is compounded from the following ingredients:

| | |
|---|---|
| N-[4″-Imidazolidinon-(2′)-yl-phenethyl]-N′-(o-ethyl-phenyl)-piperazine | 30 parts |
| Lactose | 70 parts |
| Corn starch | 93 parts |
| Secondary calcium phosphate | 47 parts |
| Soluble starch | 3 parts |
| Magnesium stearate | 3 parts |
| Colloidal silicic acid | 4 parts |
| Total | 250 parts |

Preparation:

The piperazine compound is intimately admixed with the lactose, the corn starch and the calcium phosphate, the mixture is granulated with the aid of an aqueous solution of the soluble starch in conventional fashion, and the granulate is dried and admixed with the remaining ingredients. The composition is compressed into 250 mgm-tablets in a conventional tablet making machine. Each tablet contains 30 mgm of the piperazine compound and is an oral dosage unit composition with effective CNS-depressing action.

EXAMPLE 43

Coated pills

The pill core composition is compounded from the following ingredients:

| | |
|---|---|
| N-[4″-Imidazolidinon-(2′)-yl-phenylethyl]-N′-(o-methyl-phenyl)-piperazine · HCl | 40 parts |
| Lactose | 50 parts |
| Corn starch | 80 parts |
| Secondary calcium phosphate | 50 parts |
| Magnesium stearate | 3 parts |
| Soluble starch | 3 parts |
| Colloidal silicic acid | 4 parts |
| Total | 230 parts |

Preparation:

The ingredients are compounded in the same manner as in the preceding example, the composition is compressed into 230 mgm-pill cores which are subsequently coated with a thin shell consisting essentially of a mixture of talcum, sugar and gum arabic, and the coated pills are polished with beeswax. Each pill contains 40 mgm of the piperazine compound and is an oral dosage unit composition with effective CNS-depressing action.

EXAMPLE 44

Suppositories

The suppository composition is compounded from the following ingredients:

| | |
|---|---|
| N-[4″-Imidazolidinon-(2′)-yl-phenethyl]-N′-(m-chloro-phenyl)-piperazine · $CH_3SO_3H$ | 30 parts |
| Lactose, powdered | 45 parts |
| Suppository base (e.g. cocoa butter) | 1625 parts |
| Total | 1700 parts |

Preparation:

The lactose and the piperazine compound are intimately admixed with each other, the mixture is homogeneously blended into the molten suppository base, and 1,700 mgm-portions of the composition are filled into cooled suppository molds and allowed to harden therein. Each suppository contains 30 mgm of the piperazine compound and is a rectal dosage unit composition with effective CNS-depressing action.

Analogous results are obtained when any one of the other N-phenyl-imidazolidinones embraced by formula I or a non-toxic salt thereof was substituted for the particular N-phenyl-imidazolidinone in Examples 42 through 44. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

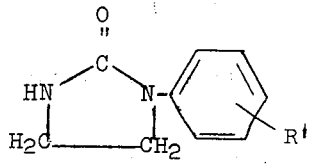

wherein
R' is in the m- or p- position and is selected from the group consisting of —CH₂—A, —CHR₁—CH₂-A and

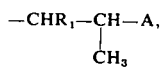

where
R₁ is hydrogen or hydroxyl, and
A is

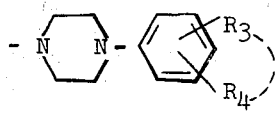

where
R₃ is hydrogen, chlorine, methyl, ethyl, trifluoromethyl or lower alkoxy, and
R₄ is hydrogen or methyl, or
R₃ and R₄, together with each other and neighboring carbon atoms of the phenyl ring to which they are attached, are naphthyl,
or a non-toxic, pharmacologically acceptable acid addition salt thereof.

2. A compound of claim 1, wherein
R' is in the m- or p- position and is selected from the group consisting of —CH₂—A, —CHR₁—CH₂-A and

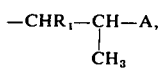

where
R₁ is hydrogen or hydroxyl, and
A is

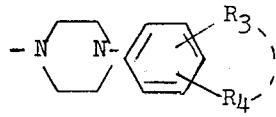

where
R₃ is hydrogen, chlorine, methyl or ethyl, and
R₄ is hydrogen or methyl, or
R₃ and R₄, together with each other and neighboring carbon atoms of the phenyl ring to which they are attached, are naphthyl,
or a non-toxic, pharmacologically acceptable acid addition salt thereof.

3. A compound of claim 2 wherein
R' is in the m- or p- position and is selected from the group consisting of —CH₂—CH₂—A and

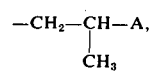

where
A is

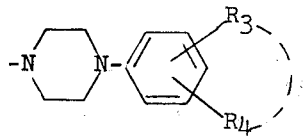

where
R₃ is hydrogen, chlorine, methyl or ethyl, and
R₄ is hydrogen or methyl, or
R₃ and R₄, together with each other and neighboring carbon atoms of the phenyl ring to which they are attached, are naphthyl,
or a non-toxic, pharmacologically acceptable acid addition salt thereof.

4. A compound of claim 1, which is N-[4''-imidazolidinon-(2')-yl-phenethyl]-N'-(o-ethylphenyl)-piperazine or a non-toxic, pharmacologically acceptable acid addition salt thereof.

5. A compound of claim 1, which is N-[4''-imidazolidinon-(2')-yl-phenethyl]-N'-(o-methylphenyl)-piperazine or a non-toxic, pharmacologically acceptable acid addition salt thereof.

* * * * *

UNITED STATES PATENT OFFICE
CERTIFICATE OF CORRECTION

Patent No. 3,937,708　　　　　　　　Dated February 10, 1976

Inventor(s) ANTON MENTRUP, ERNST-OTTO RENTH, KURT SCHROMM and PETER DANNEBERG

It is certified that error appears in the above-identified patent and that said Letters Patent are hereby corrected as shown below:

Front page, in the title　　"N-PHENYL-IMIDAZOLIDINE-1-ONES" should read -- N-PHENYL-IMIDAZOLIDINE-2-ONES --

Col. 1 in the title　　"N-PHENYL-IMIDAZOLIDINE-1-ONES" should read -- N-PHENYL-IMIDAZOLIDINE-2-ONES --

Col 27, line 56　　"EXAMPLE"" should read -- EXAMPLE 38 --

Signed and Sealed this twenty-seventh Day of April 1976

[SEAL]

Attest:

RUTH C. MASON
Attesting Officer

C. MARSHALL DANN
Commissioner of Patents and Trademarks